United States Patent [19]
van Loon

[11] Patent Number: 5,989,292
[45] Date of Patent: Nov. 23, 1999

[54] ADJUSTABLE TEMPOROMANDIBULAR SURGICAL IMPLANT

[76] Inventor: Jan-Paul van Loon, Petrus Campasingel 221, Groningen, Netherlands, 9713 AM

[21] Appl. No.: 08/860,889
[22] PCT Filed: Dec. 21, 1995
[86] PCT No.: PCT/NL95/00440
§ 371 Date: Dec. 1, 1997
§ 102(e) Date: Dec. 1, 1997
[87] PCT Pub. No.: WO96/19161
PCT Pub. Date: Jun. 27, 1996

[30] Foreign Application Priority Data

Dec. 21, 1994 [EP] European Pat. Off. .............. 94203714

[51] Int. Cl.⁶ ................................ A61F 2/30; A61F 2/28; A61F 2/02
[52] U.S. Cl. .................. 623/18; 623/16; 623/11
[58] Field of Search ............... 623/16, 18; 606/70, 606/71

[56] References Cited

U.S. PATENT DOCUMENTS

| | | | |
|---|---|---|---|
| 3,178,728 | 4/1965 | Christensen | 623/18 |
| 3,579,643 | 5/1971 | Morgan | 623/18 |
| 4,693,722 | 9/1987 | Wall | 623/18 |
| 4,778,472 | 10/1988 | Homsy et al. | 623/18 |
| 4,936,852 | 6/1990 | Kent et al. | 623/18 |
| 5,405,393 | 4/1995 | Falkenstrom | 623/18 |
| 5,549,680 | 8/1996 | Gordon | 623/18 |

*Primary Examiner*—Mickey Yu
*Assistant Examiner*—Alvin Stewart
*Attorney, Agent, or Firm*—Varnum, Riddering Schmidt & Howlett LLP

[57] ABSTRACT

A temporomandibular surgical implant includes a L-shaped bracket having first and second legs extending transversely with respect to each other. A portion of the first leg constitutes a mounting surface adapted to be mounted against an outer lateral surface of a patient's zygomatic arch. The portion of the first leg constituting the mounting surface faces in the direction in which the second leg extends away from the first leg. The implant includes a fitting member provided with a seating surface that is adapted to be seated against the articular eminence of the patient and is movably connected to the second leg in such a manner that the seating surface faces substantially in the direction in which the first leg extends away from the second leg. Since the fitting member carried by the second leg is movable, the orientation of the seating surface with respect to the mounting surface can be adjusted to the orientation of the articular eminence relative to the outer lateral surface of the zygomatic arch in a particular patient. In this configuration, the fitting member may be readily adjusted to an optimal position relative to the L-shaped bracket to provide a snug fit with the articular eminence. A single design of the mounting surface and a limited number of designs of the fitting member with hollow cylinder-sector shaped seating surfaces with different radii will readily accommodate the zygomatic arches of a number of different patients. The fitting member is detachably connected to the bracket and is rotatable relative to the bracket.

31 Claims, 9 Drawing Sheets

ADJUSTABLE TEMPOROMANDIBULAR SURGICAL IMPLANT

The invention relates to a temporomandibular surgical implant comprising an L-shaped bracket having a first and a second leg extending transversely with respect to each other, wherein a portion of the first leg constitutes a mounting surface adapted to be mounted against an outer lateral surface of a patient's zygomatic arch, the mounting surface facing in a direction in which the second leg extends away from the first leg. More in particular, the invention relates to a temporomandibular joint prosthesis comprising such a temporomandibular surgical implant. Such an implant and such a prosthesis are known from U.S. Pat. No. 4,917,701.

A major problem associated with the use of temporomandibular surgical implants is to obtain a good fit between the temporal implant and the patient's bone structure. Many proposals have been made thus far to solve this problem.

In U.S. Pat. No. 3,597,643 a metallic articular eminence implant is disclosed which covers only the articular eminence of the temporal component of the joint. A good fit of the implant cannot always be achieved without surgical shaving of the eminence, even when a variety of implants of about at least ten sizes per side are available. Apart from the costs associated with providing such a number of implants ready for implantation (i.e. clean and sterilized), each time a patient is treated, the necessity of having to select the best design from such a number of implants during the surgical operation is cumbersome and difficult because the bone structure to which the implant has to be fitted is not well visible.

From the above-mentioned U.S. Pat. No. 4,917,701 an implant is known which comprises a rigid plate of which a part adapted to cover the mandibular fossa portion of the glenoid fossa is provided with a resilient layer to obtain a better fit to the mandibular fossa portion of the glenoid fossa and a more uniform distribution of loads. In implanted condition, this implant exerts considerable forces onto the fossa. However, the fossa is not suitable to bear such forces because the bone structures of the fossa are very thin. Furthermore, fitting this known implant to the articular eminence and to the zygomatic arch is as problematic as in the previously described implant.

Another known approach is to determine the shape of the bone structure against which the implant is to be seated, in particular of the articular eminence, before surgical treatment. To obtain information regarding the shape of the relevant bone structure, CT-scans or X-ray pictures are made. On the basis of these scans a model is prepared to which the implant is custom-fitted. Although this approach is theoretically very promising, in practice a satisfactory fit is often not obtained, mainly because of a lack of accuracy, in particular where the surfaces of the bone structure are irregular and/or thin. Another disadvantage of custom-fitting is that it is very expensive and time consuming. During X-raying for obtaining information regarding the shape of the bone structure to which the implant is to be fitted, a patient is subjected to substantial irradiation doses.

It is an object of the present invention to provide a temporomandibular implant which provides an improved fit for a wide variety of patients, in a reduced variety of sizes and designs, which is easy to implant and entails substantially less cost than custom-fitting.

According to the present invention, this object is achieved by providing an implant of the type indicated in the opening paragraph hereof, with the characterizing features that the implant further comprises a fitting member having a seating surface which is adapted to be seated against the articular eminence of the patient in mounted position of the implant and that the fitting member is movably connected to the second leg in such a manner that in all possible positions of the fitting member relative to the bracket the seating surface faces at least substantially in a direction in which the first leg extends away from the second leg.

Since the fitting member carried by the second leg is movable, the orientation of its seating surface with respect to the mounting surface can be adjusted to the orientation of the articular eminence relative to the outer lateral surface of the zygomatic arch in a particular patient. During surgery, if the mounting surface is mounted against the zygomatic arch, the fitting member will automatically find itself an optimal position relative to the bracket to provide a snug fit with the articular eminence. Moreover, surgery will be relatively easy because the seating surface will always face at least substantially in a direction in which the first leg extends away from the second leg.

Furthermore, the individual articular eminences and outer lateral surfaces of zygomatic arches of different patients show relatively little variation in shape, the articular eminence generally being shaped as a cylinder section. Therefore, a limited variation in shapes and dimensions of the mounting surface and the seating surface is sufficient to accommodate to a wide variety of patients. In particular, a single design of the mounting surface and a limited number of designs of fitting members with hollow cylinder-sector shaped seating surfaces with different radii will be sufficient.

According to a special embodiment of the invention, the fitting member is detachably connected to the second leg. This means that the bracket may be provided with a selectable fitting member which will provide an optimal snug fit with the articular eminence.

According to an advantageous embodiment of the invention, the fitting member is rotatable relative to the second leg around an axis of rotation which extends (substantially parallel to the mounting surface) in a direction in which the first leg extends away from the second leg. By providing the fitting member with at least such a degree of freedom of motion relative to the bracket, it is experienced that a generally snug fit of the implant to the patient's skull will be provided.

Below, embodiments of the invention for a right halve of a patient's skull are described in more detail with reference to the accompanying drawings, in which.

In the drawings, corresponding parts of different embodiments are designated by mutually identical reference numerals.

Figure 5:
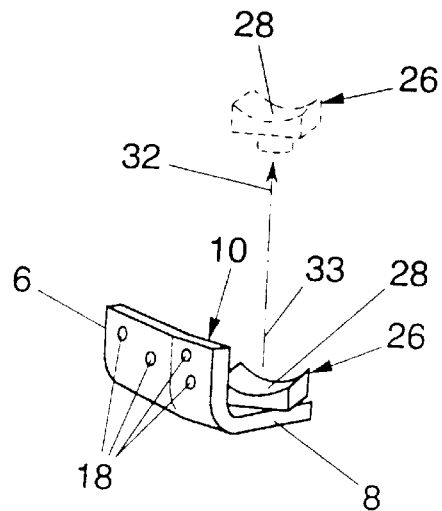
FIG. 5 is a perspective view of the implant according to FIGS. 1–4.
Figure 6:
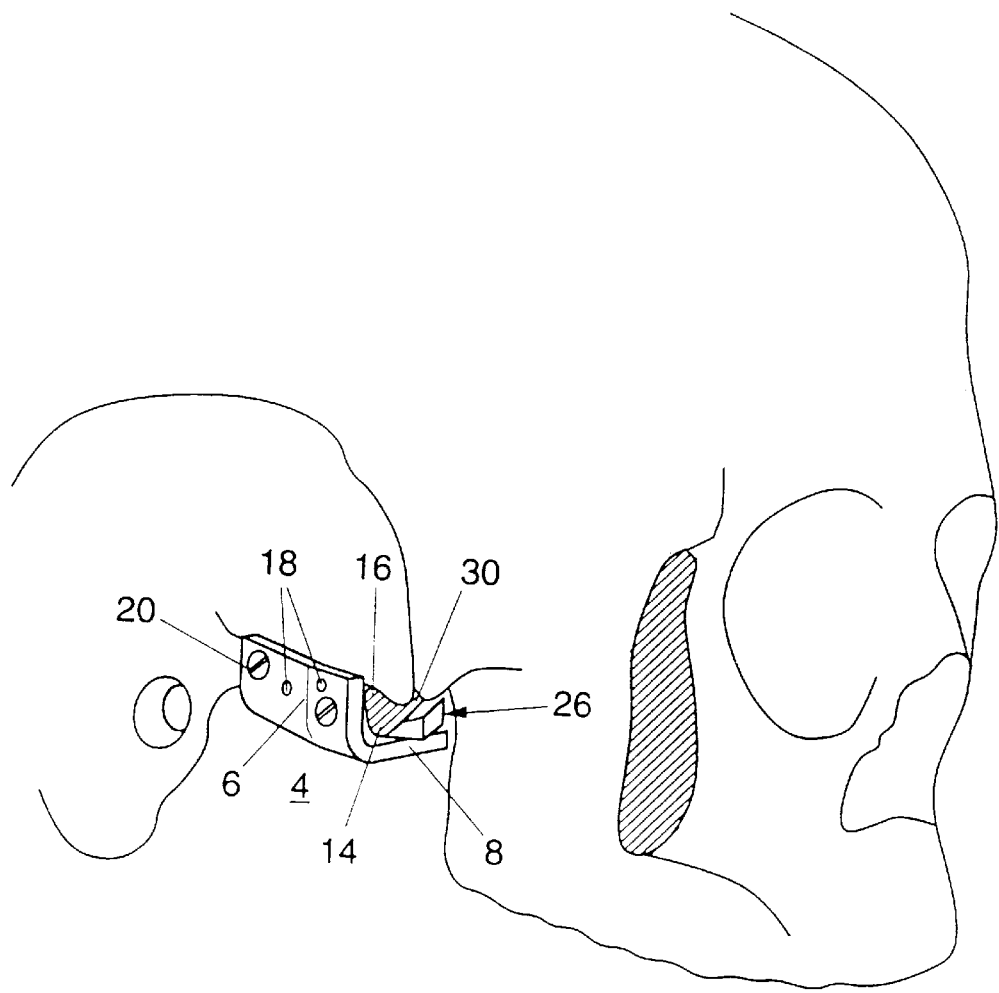
FIG. 6 is a cut-away perspective view of a human skull with an implant according to FIGS. 1–4 in implanted condition.

The invention will first be described with reference to a most preferred embodiment. FIGS. 1–4 respectively show from different angles a complete right sided temporomandibular joint prosthesis 1 comprising a temporomandibular surgical implant 2 according to the preferred embodiment of the invention. The roman numerals I–IV corresponding to the figure numbers 1–4 indicate the angles from which the prosthesis is shown in these figures. FIGS. 5 and 6 show the temporomandibular surgical implant 2 of FIGS. 1–4 individually without the remaining members of the complete joint prosthesis.

The temporomandibular surgical implant 2 comprises an L-shaped bracket 4 having a first leg 6 and a second leg 8, which legs extend transversely with respect to each other. A portion 10 of the first leg 6 constitutes a mounting surface 12 adapted to be mounted against an outer lateral surface 14 (FIGS. 1, 2, 6) of a patient's zygomatic arch 16. The mounting surface 12 faces in a direction in which the second leg 8 extends away from the first leg 6. The first leg 6 is provided with a plurality of holes 18 (FIG. 5) for bone screws 20 (FIG. 6) of which suitable ones may be selected depending on the relative positions of the mounting surface 12 and the patient's zygomatic arch 16. The mounting surface 12 may be slightly curved (see FIG. 4, reference numeral 22) around an axis 11 which is parallel to the direction in which the first leg 6 extends away from the second leg 8 or around an axis perpendicular to leg 6 as well as leg 8, to accommodate to current shapes of zygomatic arches 16. Together the first leg 6 and the second leg 8 constitute an essentially L-shaped, metallic bracket 4, which is preferably made of a biocompatible metal such as, for example, titanium alloy. However, the first leg 6 can also be a separate part connected to the second leg 8 and either the first leg 6 or the second leg 8 or both can be incorporated into a bearing member (not shown) of a temporal component of a total temporomandibular joint prosthesis 1.

In the embodiment of FIGS. 1–4 the bracket 4 further comprises a stopping flange 24 for mounting and fixating a temporal component.

The implant 2 further comprises a fitting member 26 having a seating surface 28 which is adapted to be seated against the articular eminence 30 (FIGS. 1, 2, 6) of the patient if the implant 2 is in its mounted position. The fitting member 26 is movably connected to the second leg 8 in such a way that in all possible positions of the fitting member 26 relative to the bracket 4 the seating surface 28 faces at least substantially in a direction 32 (FIG. 5) in which the first leg 6 extends away from the second leg 8. According to the preferred embodiment the fitting member 26 is rotatable relative to the second leg 8 around an axis of rotation 33 (FIG. 5) which extends at least substantially in the direction 32 in which the first leg 6 extends away from the second leg 8.

The seating surface 28 is preferably concave. According to the preferred embodiment the seating surface 28 is cylindrically shaped. Hence the fitting member 26 forms a shallow gully. The direction of the normal to the seating surface 28 at the point where the axis of rotation 33 intersects the seating surface 28 is substantially parallel to the axis of rotation 33. As will become clear from other possible embodiments to be discussed later, this is not absolutely necessary.

The complete temporomandibular joint prosthesis 1 as shown in FIGS. 1–4 comprises a temporal component 34 and a mandibular component 36, which is pivotable with respect to the temporal component 34 when the prosthesis is in the implanted condition as shown. The mandibular component 36 is provided with a ball 38 which is rotatably seated in a cavity of the temporal prosthesis component 34. The mandibular prosthesis component 36 is attached to the mandible of which the natural contour is shown by dashed lines 40.

The second leg 8 constitutes a second mounting surface 42 which is adapted to be mounted against the temporal prosthesis component 34 for swivelling cooperation with the mandibular prosthesis component 36 when in the implanted condition wherein the second mounting surface 42 faces away from the direction in which the first leg 6 extends away from the second leg 8. The temporal prosthesis component 34 may be mounted, for example, abutting to the mounting flange 24.

Because the fitting member 26 carried by the second leg 8 is rotatable, the orientation of its seating surface 28 with respect to the bracket 4 can be adjusted to the particular patient's orientation of the articular eminence 30 relative to the outer lateral surface 14 of the zygomatic arch 16. Thereby the implant 2 has—in accordance with the invention—the ability to adjust itself (by rotating the fitting member 26) to the specific dimensions of the patient's skull so that a snug and stable fit between the mounting surface 12 and the outer lateral surface 14 on the one hand and the seating surface 28 and the eminence 30 on the other hand is obtained. Moreover, surgery is relatively easy because the seating surface will always face at least substantially in a direction in which the first leg 6 extends away from the second leg 8. This will be further explained with reference to FIGS. 7 and 8.

The articular eminence 30 is generally shaped as an inferior section of a circumferential surface of a cylinder, i.e. curved essentially in one direction and with a uniform radius of curvature around a single axis 50. The orientation of the articular eminence 30 relative to the outer lateral surface 14 of the zygomatic arch 16 can for example be characterized by projections $\alpha_{x,y}$ and $\alpha_{y,z}$, respectively. The projection $\alpha_{x,y}$ indicates the projection of the angle $\alpha$ between the axis 50 of curvature of the articular eminence 30 and a plane 52 defined by the lateral outside of the zygomatic arch 16 onto a horizontal plane x,y. The projection $\alpha_{y,z}$ indicates the projection of the angle α onto a vertical transversal plane. The orientations "horizontal" and "vertical" are to be understood, respectively, as horizontal and vertical relative to the earth if the patient is in a natural standing or sitting position looking in a horizontal direction.

The fitting member 26 of the implant as shown in FIGS. 1–6 is rotatable around the axis 33 intersecting substantially the centre of the seating surface 28 of the fitting member 26. Thus, in mounted condition, the axis 33 is directed substantially parallel to the plane 52 and perpendicular to the axis 50. Therefore, rotation of the fitting member 26 around the axis 33 provides an adjustability of the orientation of the seating surface 28 of the fitting member 26 to the angle $α_{x,y}$. This adjustment is possible for interpatient variations of the angle α between the articular eminence 30 and the outer lateral surface 14 of the zygomatic arch 16. Since the seating surface 28 is formed as a shallow gully, the orientation of the fitting member 26 relative to the cylinder section shaped articular eminence 30 is self-adjusting.

During surgery the surgeon will rotate the fitting member 26 in what he feels at first sight will be the position which best fits the dimensions of the patient's skull before the implant 2 is actually placed into its mounting position. After that, the implant 2 will be placed into its mounted position. If the fitting member 26 is not in the optimal position it will automatically rotate further to its optimal position due to forces acting between the seating surface 28 and the articular eminence 30. The curved seating surface 28 will provide a stable balance in this respect.

Figure 1:
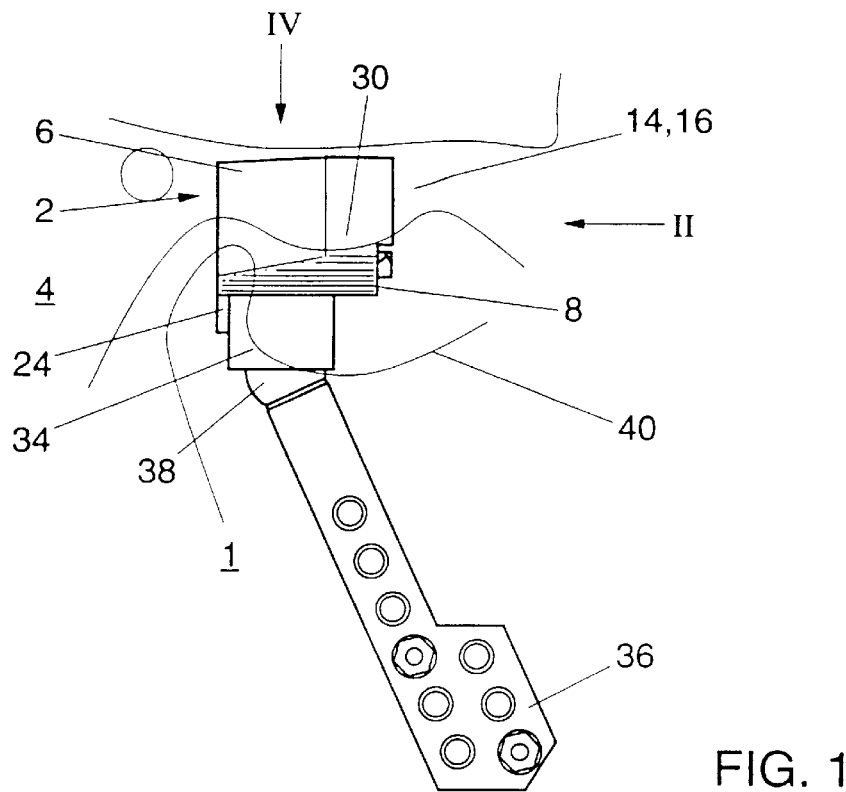
FIGS. 1–4 show perspective views from different angles of a complete temporomandibular joint prosthesis comprising an adjustable temporomandibular implant according to the present invention.
Figure 2:
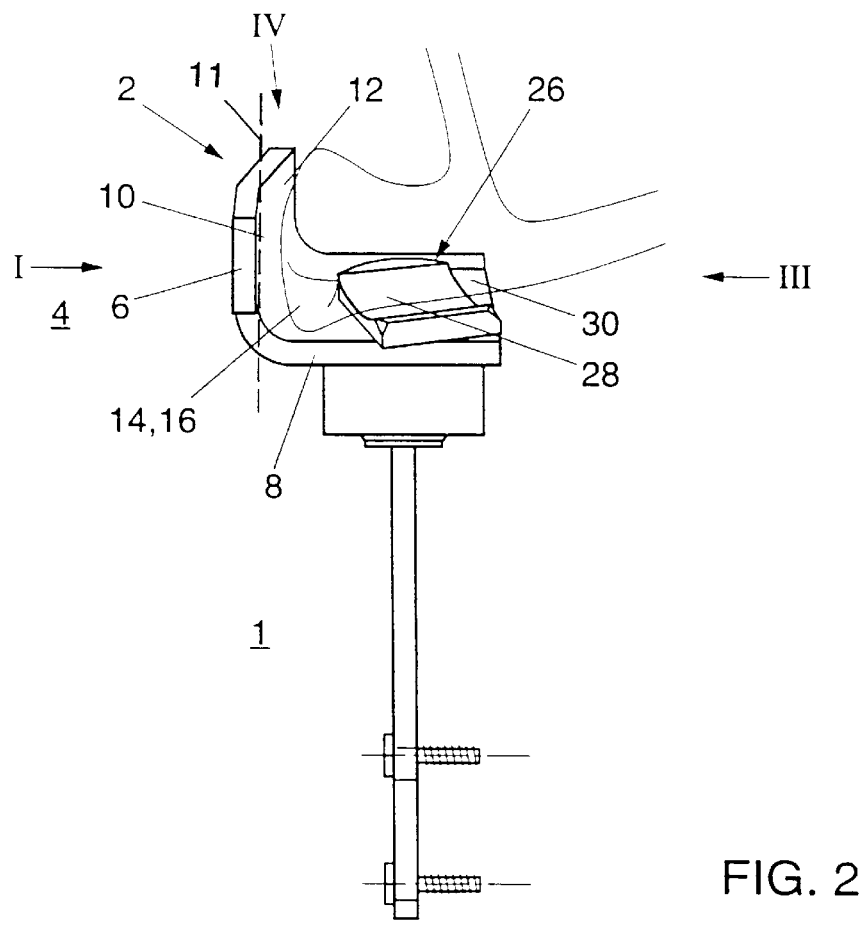
Figure 3:
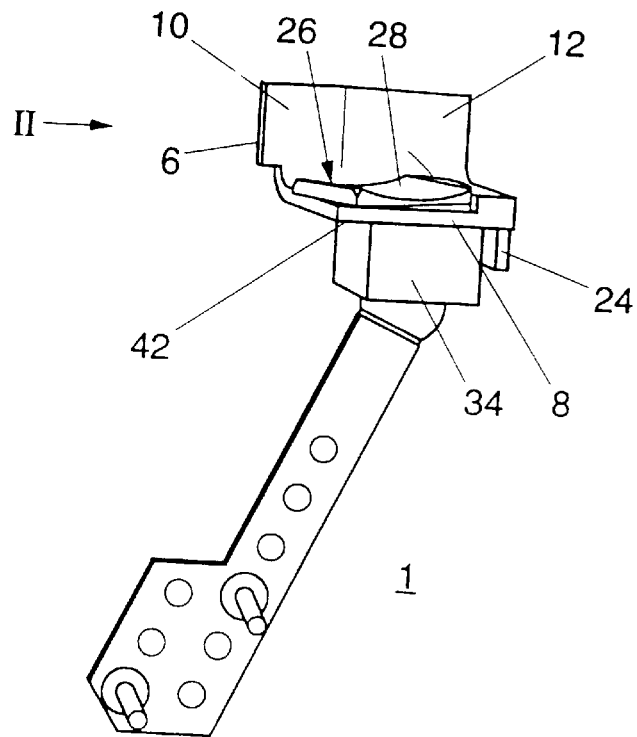
Figure 4:
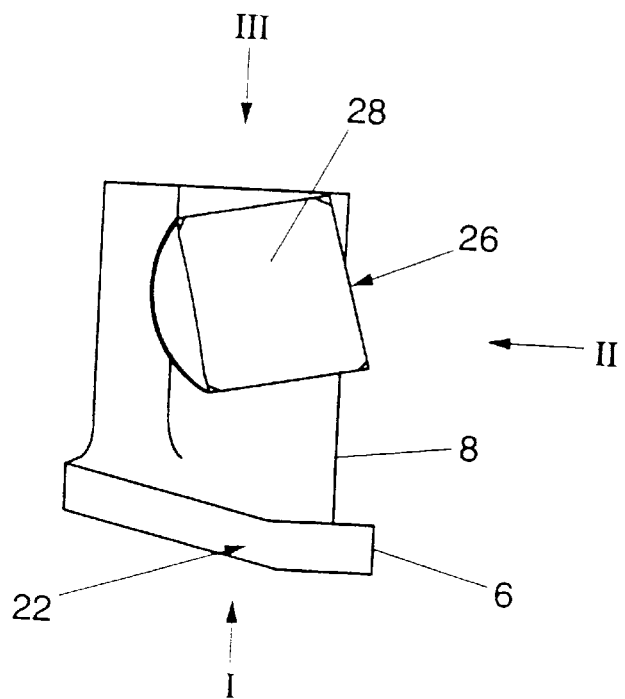

As appears particularly clearly from FIGS. 1, 2, in implanted condition, the cylindrically shaped seating surface 28 partially encloses the articular eminence 30, so in implanted condition the fitting member 26 is reliably locked in place relative to the articular eminence 30.

Since the vertical dimensions of the outer lateral surface 14 of the zygomatic arch 16 are usually small compared with its horizontal dimensions, parallelism in the vertical direction between the outer lateral surface 14 and the mounting surface 12 of the first leg 6 is generally not very critical. This means that the single degree of freedom of motion of the fitting member 26 about the axis of rotation 33 will generally be sufficient to obtain a good fit of the implant to the patient's bone structure.

Moreover, by slightly turning the implant 2 around a horizontal axis transverse to the zygomatic arch 16, generally a position can be found in which the implant 2 can be accommodated to both the projections $α_{x,y}$ and $α_{y,z}$, respectively. In surgical practice this can simply be achieved by rotating the implant 2 in the plane 52 while keeping the mounting surface 12 urged against the outer lateral surface 14 of the zygomatic arch 16 and keeping the seating surface 28 urged against the articular eminence 30 until one feels that a stable seating is achieved. Then the implant 2 can be fixed to the zygomatic arch 16 using the bone screws 20.

Thus, a very good adjustability of the implant to interpatient variations in relevant parts of the bone structure can be achieved with a single degree of freedom of motion of the fitting member 26 relative to the mounting surface 12, being the freedom of rotary motion.

According to another aspect of the invention the fitting member 26 is detachably connected to the second leg 8 (see FIG. 5). This implies that a fitting member 26 having a fitting surface 28 which best suits the dimensions of the patient's articular eminence 30 may be selected and subsequently connected to the bracket 4.

Thus a further improved fit of the implant can be achieved by selecting a fitting member with a seating surface 28 closely fitting the shape of the patient's articular eminence 30. Since the only variable with respect to which available fitting members generally have to differ from each other is the width of the gully and/or its radius of curvature, a limited number of fitting members 26 is sufficient to obtain a very good fit to the articular eminence 30 of almost any patient. Moreover, selecting as to the quality of fit with respect to a single parameter is very simple and can be accomplished easily and quickly in the course of surgical treatment.

Such articular eminences 30 and lateral outer surfaces 14 of zygomatic arches 16 of different patients show relatively little variation in shape, the articular eminence generally being shaped as a cylinder section. Therefore, a limited variation in shapes of the mounting surface 12 and the seating surface 28 is sufficient to accommodate to the bone structures of a wide variety of patients. In particular, a single design of the mounting surface 12 and a limited number of designs of fitting members 26 with hollow cylinder-sector shaped seating surfaces 28 with different radii will be sufficient.

Such a seating surface may also comprise a number of flat surface segments which form the concave seating surface.

According to a relevant feature of the invention, the size of the fitting member 26 is adapted in such a manner that there exists a free space between the first leg 6 and the fitting member 26 for all possible positions of the fitting member 26 relative to the bracket 4. This free space will provide an accommodation space for a rather prominent part 31 (FIG. 8) of the lateral portion of the eminence 30.

As will be apparent to the skilled man in the art, there are many suitable embodiments of the implant 2 having a fitting member 26 which is movably connected to the bracket 4. Without going into detail, a number of such possible embodiments will be briefly discussed below.

Figure 9:
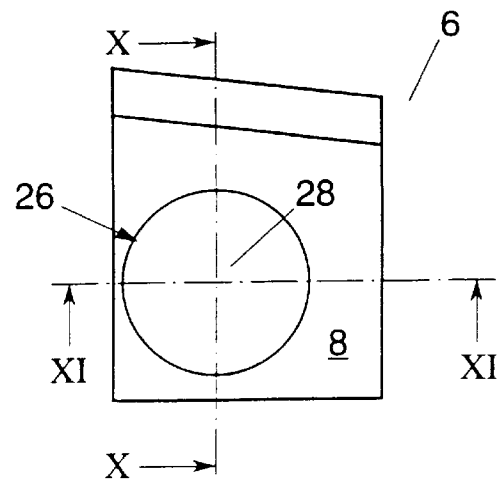
FIG. 9 is a schematical top plan view of a second embodiment of an implant according to the present invention.
Figure 10:
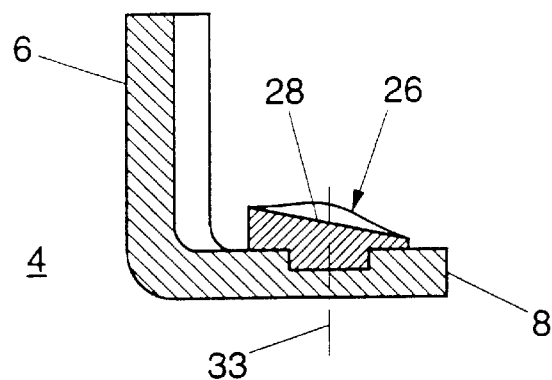
FIG. 10 is a cross-sectional view along line X—X in FIG. 9.
Figure 11:
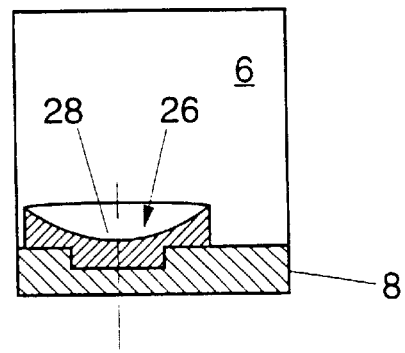
FIG. 11 is a cross-sectional view along line XI—XI in FIG. 9.
Figure 12:
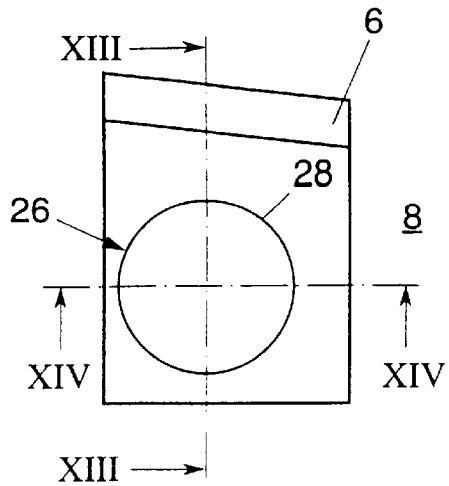
FIG. 12 is a schematical top plan view of a third embodiment of an implant according to the present invention.
Figure 13:
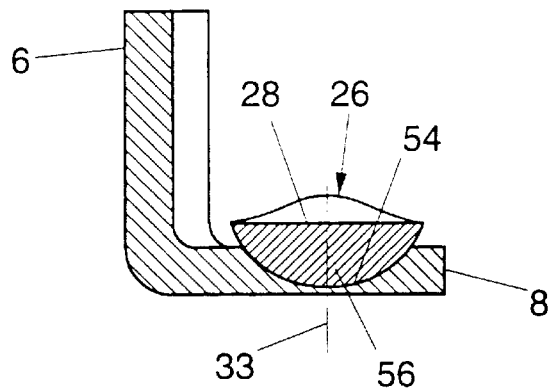
FIG. 13 is a cross-sectional view along line XIII—XIII in FIG. 12.
Figure 14:
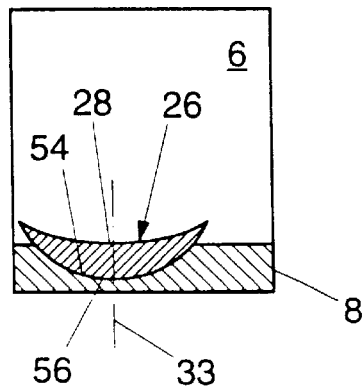
FIG. 14 is a cross-sectional view along line XIV—XIV in FIG. 12.

In the implant shown in FIGS. 9–11, the fitting member 26 is also rotatable around the axis 33. However, the side of the fitting member 26 facing the second leg 8 is of simpler design since the fitting member 26 is formed as a section of a cylindrical rod. Such a fitting member 26 can be efficiently manufactured from a cylindrical rod. Furthermore, the longitudinal axis of the gully formed by the seating surface 28 is not oriented perpendicularly but obliquely relative to the axis 33. In other words, the normal to the seating surface 28 at the point where the axis 33 intersects the seating surface 28 makes an angle with the axis 33. Preferably, such an angle will be smaller than 15°. By rotating the fitting member 26 over 180°, a different orientation of the longitudinal axis of the gully relative to the mounting surface 12 is obtained. This is particularly suitable for adjusting the implant 2 to different angles $α_{y,z}$, as seen in FIG. 7.

Referring now to FIGS. 1–4 and 12–14, there is shown an implant provided with a fitting member 26 which is rotatable about the axis 33 intersecting the seating surface 28. In addition, the second leg 8 is provided with a spherical cavity 54 in which a corresponding convex spherical part 56 of the fitting member 26 is seated. In other words, a normal to the seating surface 28 is adjustable relative to a normal to the mounting surface 12. Thus, the fitting member 26 is tiltable in any direction, so that a perfect fit can be obtained for virtually any patient.

Figure 7:
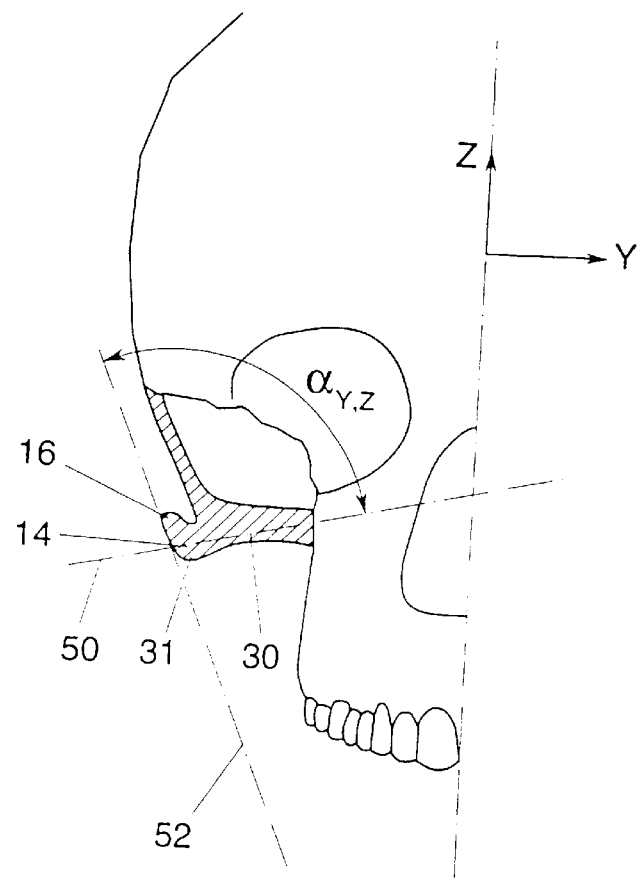
FIG. 7 is a cut-away frontal view of a right half of a human skull.
Figure 8:
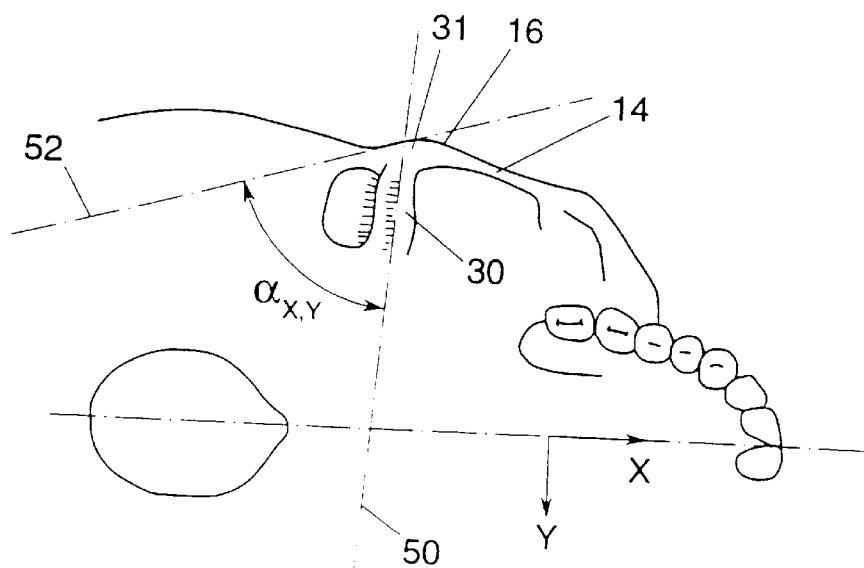
FIG. 8 is a caudal view of a front part of a right half of a human skull.

By tilting the fitting member 26 in a plane intersecting the first leg 6, the implant adjusts in particular to different angles $α_{y,z}$, as seen in FIG. 7.

Referring to FIGS. 1–6 and FIGS. 21–23, tilting the implant 2 about an axis extending transversely to the mounting surface 12 essentially results in anterior or posterior displacement of the fitting member 26. This is mainly useful for intended mounting positions of the mounting surface 12 against the outer lateral surface 14 of the zygomatic arch 16.

Figure 21:
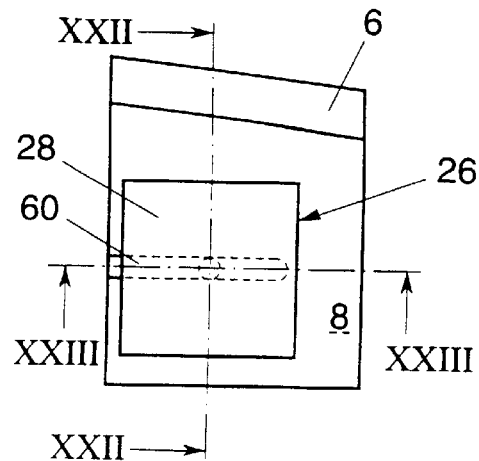
FIG. 21 is a schematical top plan view of a sixth embodiment of an implant according to the present invention.
Figure 22:
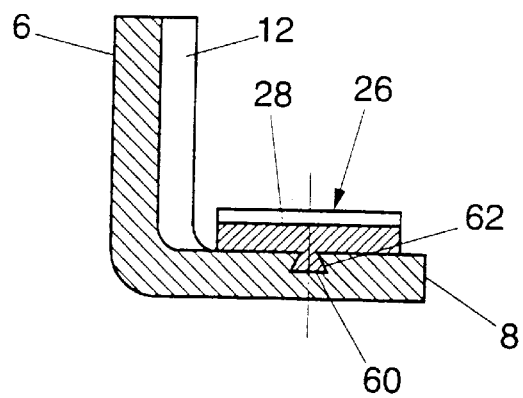
FIG. 22 is a cross-sectional view along line XXII—XXII in FIG. 21.
Figure 23:
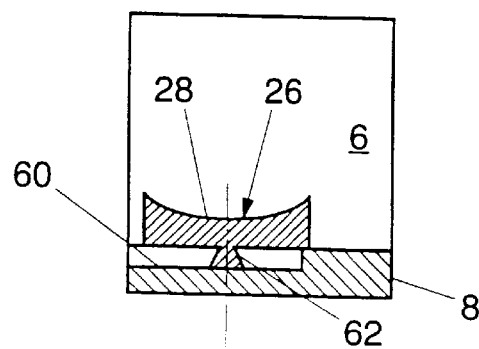
FIG. 23 is a cross-sectional view along line XXIII—XXIII in FIG. 21.

A similar effect can also be achieved if the fitting member 26 is movable back and forth relative to the bracket 4 in a direction Z—Z which is substantially perpendicular to the respective directions in which the first and second legs 6, 8 extend away from each other respectively. The implant shown in FIGS. 21–23 provides for this possibility. To achieve this possibility of displacement of the fitting member 26, the implant 2 is provided with a groove 60 extending in a direction which is at least substantially perpendicular to the directions in which the first and second legs 6, 8 extend away from each other respectively.

The groove 60 is dovetail-shaped and the fitting member 26 is provided with a truncated conical member 62 of which the diameter corresponds to the profile of the groove 60. Thus, the fitting member 26 is restrained from displacement in the direction in which the seating surface 26 faces. In other words the fitting member is restrained from movement in the direction in which the first leg 6 extends away from the second leg 8. This is advantageous for avoiding inadvertent dislocation of the fitting member 26 during surgical implantation.

The position of the fitting member 26 can also be movable in a direction towards and away from the first leg 6. In practice this allows for the seating surface 28 to be moved along the longitudinal axis 50 of the articular eminence 30 to find a position where it fits the articular eminence best. Such lateral adjustability of the position of the fitting member 26 can for example be achieved by providing an implant similar to the implant shown in FIGS. 21–23, but in which the groove 60 extends transversely to the mounting surface 12.

Figure 15:
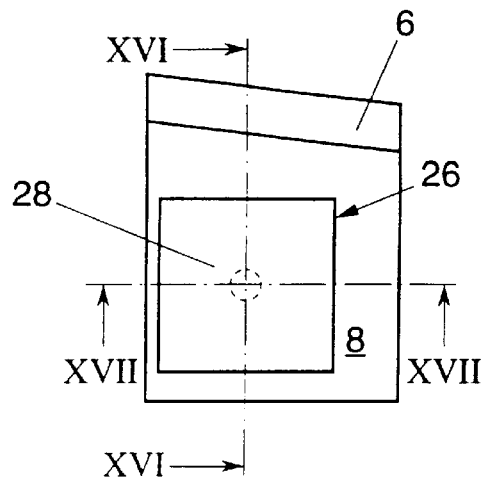
FIG. 15 is a schematical top plan view of a fourth embodiment of an implant according to the present invention.
Figure 16:
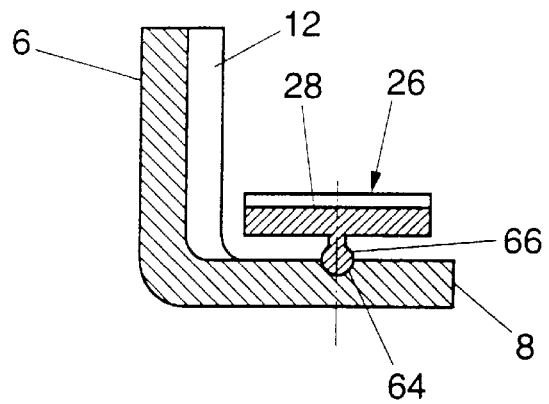
FIG. 16 is a cross-sectional view along line XVI—XVI in FIG. 15.
Figure 17:
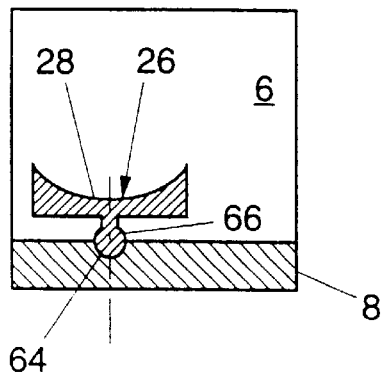
FIG. 17 is a cross-sectional view along line XVII—XVII in FIG. 15.

The fitting member 26 of the implant shown in FIGS. 15–17 is also tiltable in any direction. Similarly to the implant shown in FIGS. 12–14, the second leg 8 is provided with a spherical recess 64 and the fitting member 26 is provided with a spherical surface 66, with a radius providing a sliding fit within the spherical recess 64. However, the spherical surface 66 has a relatively small diameter and is positioned in spaced relation away from the seating surface 28. Thereby the centre of rotation of the tilting movement is also positioned in spaced relation below the seating surface 28. As a result, during tilting, the seating surface 28 moves in the direction in which it tilts so that a particularly effective adjustability along five degrees of freedom of motion is obtained. However, the implant will still provide a stable fit in the implanted condition because it allows for only a relatively small adjustability of the seating surface 28 in the direction in which the first leg 6 extends away from the second leg 8.

If the position of the seating surface 28 is adjustable in this direction, optimum adjustments to various vertical positions of the articular eminence 30 relative to the outer lateral surface 12 of the zygomatic arch 16, i.e. to variations in height or thickness of the articular eminence 30 and to curvature of the zygomatic arch 16, can be achieved.

Figure 18:
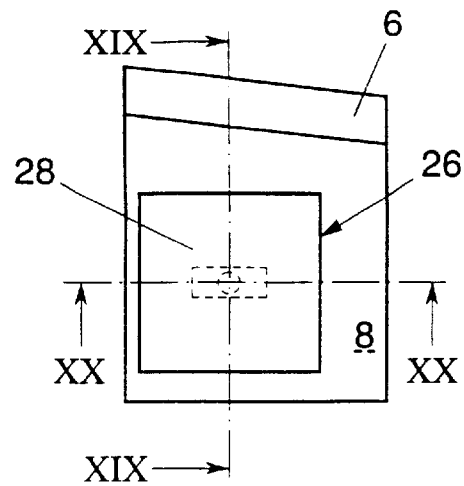
FIG. 18 is a schematical top plan view of a fifth embodiment of an implant according to the present invention.
Figure 19:
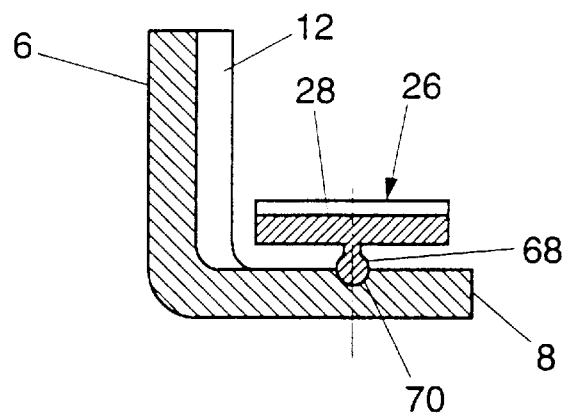
FIG. 19 is a cross-sectional view along line XIX—XIX in FIG. 18.
Figure 20:
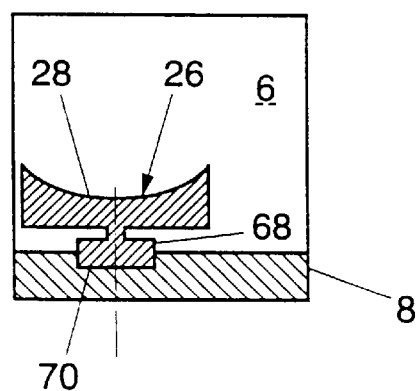
FIG. 20 is a cross-sectional view along line XX—XX in FIG. 18.

The fitting member 26 of the implant shown in FIGS. 18–20 is guided to be tiltable only around an axis which is transverse to the directions in which the first and second legs 6, 8 extend away from each other respectively. Such a design is particularly advantageous where adjustment to the angle $\alpha_{y,z}$ to provide optimal fixation of the implant is desired. To obtain maximal fixation other degrees of freedom of movement of the fitting member 26 than tilting transversely to the fitting member are precluded by providing the fitting member 26 with a cylindrical member 68 spaced below the seating surface 28 and a corresponding cylindrical recess 70 in which the cylindrical member 68 is lodged.

For some patients, further degrees of freedom of motion will provide a further improved fit of the implant. However, further degrees of freedom may result in a less stable positioning of the implant 2. Nevertheless, further or other degrees of freedom of motion can be particularly advantageous for adjustment to particular interpatient variations in the structure and the relative positions and orientations of the lateral outside of the zygomatic arch 16, and the articular eminence 30. To avoid an instable fixation of the implant due to particular degrees of freedom of motion, means (not shown) may be provided for fixing the fitting member 26 to the L-shaped bracket 4 after its position has been adjusted to the bone structure of the patient.

These and other variations are all considered to fall within the scope of the invention.

I claim:

1. A temporomandibular surgical implant comprising a L-shaped bracket having a first and a second leg extending transversely with respect to each other, wherein a portion of the first leg constitutes a mounting surface adapted to be mounted against an outer lateral surface of a patient's zygomatic arch, the mounting surface facing in a direction in which the second leg extends away from the first leg, the implant further comprising a fitting member having a seating surface which is adapted to be seated against the articular eminence of the patient in mounted position of the implant and wherein the fitting member is movably connected to the second leg in such a way that in all possible positions of the fitting member relative to the bracket the seating surface faces at least substantially in a direction in which the first leg extends away from the second leg.

2. A temporomandibular surgical implant according to claim 1, wherein the fitting member is detachably connected to the second leg.

3. A temporomandibular surgical implant according to claim 1 wherein the fitting member is rotatable relative to the second leg around an axis of rotation which extends at least substantially in a direction in which the first leg extends away from the second leg.

4. A temporomandibular surgical implant according to claim 3, wherein the axis of rotation intersects the fitting member at substantially the centre of the seating surface.

5. A temporomandibular surgical implant according to claim 1, wherein the seating surface is concave.

6. A temporomandibular surgical implant according to claim 5, wherein the seating surface has the shape of a part of a cylinder.

7. A temporomandibular surgical implant according to claim 3, wherein the direction of the normal to the seating surface at the point where the axis of rotation intersects the seating surface is at least substantially parallel to the axis.

8. A temporomandibular surgical implant according to claim 3, wherein the normal to the seating surface at the point where the axis of rotation intersects the seating surface makes an angle with the axis of rotation.

9. A temporomandibular surgical implant according to claim 1, wherein the size of the fitting member is adapted in such a way that a free space exists between the first leg and the fitting member for all possible positions of the fitting member relative to the bracket.

10. A temporomandibular surgical implant according to claim 1, wherein the mounting surface is curved around an axis which is parallel to the direction in which the first leg extends away from the second leg.

11. A temporomandibular surgical implant according to claim 1, wherein the fitting member is movable in such a way that a normal to the seating surface is adjustable relative to a normal to the mounting surface.

12. A temporomandibular surgical implant according to claim 1, wherein the fitting member is movable back and forth relative to the bracket in a direction which is at least substantially perpendicular to the direction in which the first leg extends away from the second leg and the direction in which the second leg extends away from the first leg.

13. A temporomandibular surgical implant according to claim 1, wherein the fitting member is movable towards and away from the first leg.

14. A temporomandibular surgical implant according to claim 1, wherein the fitting member is restrained from movement in the direction in which the first leg extends away from the second leg.

15. A temporomandibular surgical implant according to claim 1, wherein the second leg comprises a second mounting surface which is adapted to be mounted against a temporal prosthesis component for swivelling cooperation with a mandibular prosthesis component when in implanted condition, the second mounting surface facing away from the direction in which the first leg extends away from the second leg.

16. A temporomandibular joint prosthesis comprising a temporomandibular surgical implant according to claim 1.

17. A temporomandibular joint prosthesis comprising:
a L-shaped bracket having a first leg extending in a first direction and a second leg extending in a second direction extending transversely to the first direction;
the first leg comprising a mounting surface facing in the second direction and adapted to be mounted against an outer lateral surface of a zygomatic arch of a patient;
a fitting member comprising a seating surface adapted to be seated against an articulate eminence of a patient and facing in the first direction;
the fitting member movably connected to the second leg such that in various positions of the fitting member relative to the bracket, the seating surface faces substantially in the first direction and away from the second leg.

18. The prosthesis, in accordance with claim 17, wherein the fitting member is detachably connected to the second leg.

19. The prosthesis, in accordance with claim 17, wherein the fitting member is rotatably mounted on the second leg for rotation about an axis of rotation extending in the first direction.

20. The prosthesis, in accordance with claim 19, wherein the seating surface has a geometric center and the axis of rotation intersects the fitting member substantially at the center of the seating surface.

21. The prosthesis, in accordance with claim 17, wherein the seating surface is concave.

22. The prosthesis, in accordance with claim 21, wherein the seating surface has a shape corresponding to a cylindrical surface section.

23. The prosthesis, in accordance with claim 19, wherein a line extending perpendicular to the seating surface at a point where the axis of rotation intersects the seating surface extends in a direction substantially parallel to the axis of rotation.

24. The prosthesis, in accordance with claim 19, wherein a line extending perpendicular to the seating surface at a point wherein the axis of rotation intersects the seating surface forms an oblique angle with the axis of rotation.

25. The prosthesis, in accordance with claim 17, wherein the fitting member is spaced apart from the first leg for all possible positions of the fitting member relative to the L-shaped bracket.

26. The prosthesis, in accordance with claim 17, wherein the mounting surface is curved relative to an axis extending in a direction parallel to the first direction.

27. The prosthesis, in accordance with claim 17, wherein the fitting member is movable relative to the mounting surface such that an axis extending perpendicular to the seating surface is adjustable relative to an axis extending perpendicular to the mounting surface.

28. The prosthesis, in accordance with claim 17, wherein the fitting member is movable relative to the L-shaped bracket in a direction extending perpendicularly to the first direction and perpendicular to the second direction.

29. The prosthesis, in accordance with claim 17, wherein the fitting member is movable in a direction extending parallel to the first direction.

30. The prosthesis, in accordance with claim 17, wherein the fitting member is restrained from movement in the first direction.

31. The prosthesis, in accordance with claim 17, wherein the second leg comprises a mounting surface adapted to be mounted against a temporal prosthesis component for swiveling cooperation with a mandibular prosthesis component, the second surface facing away from the first direction.

* * * * *